United States Patent [19]

Kimura et al.

[11] Patent Number: 5,227,398

[45] Date of Patent: Jul. 13, 1993

[54] BENZODIOXOLE DERIVATIVES AND HEPATOPATHY IMPROVERS COMPRISING THE SAME

[75] Inventors: Masayuki Kimura; Shouichi Nishida; Shigefumi Takeda; Kunio Hosaka, all of Ami, Japan

[73] Assignee: Tsumura & Co., Tokyo, Japan

[21] Appl. No.: 798,202

[22] Filed: Nov. 26, 1991

[30] Foreign Application Priority Data

Nov. 26, 1990 [JP] Japan .................. 2-324403
Nov. 30, 1990 [JP] Japan .................. 2-329486

[51] Int. Cl.$^5$ .................. A61K 31/36; C07D 317/48
[52] U.S. Cl. .................. 514/430; 549/436; 549/89; 549/39; 549/22; 549/21; 514/436; 514/440; 514/464
[58] Field of Search .................. 549/21, 22, 436, 39, 549/89; 514/464, 436, 440, 430

[56] References Cited

U.S. PATENT DOCUMENTS

| | | |
|---|---|---|
| 3,637,687 | 1/1972 | Chow . |
| 3,761,482 | 9/1973 | Nakagome et al. . |
| 3,914,428 | 10/1975 | Wilbur et al. . |
| 4,668,799 | 5/1987 | Yoshizawa et al. . |

FOREIGN PATENT DOCUMENTS

| | | |
|---|---|---|
| 0052887 | 6/1982 | European Pat. Off. . |
| 0099329 | 1/1984 | European Pat. Off. . |
| 0123386 | 10/1984 | European Pat. Off. . |
| 0188805 | 7/1986 | European Pat. Off. . |
| 0277091 | 8/1988 | European Pat. Off. . |
| 1336913 | 11/1973 | United Kingdom . |
| 1341401 | 12/1973 | United Kingdom . |
| 1401806 | 7/1975 | United Kingdom . |

OTHER PUBLICATIONS

Patent Abstracts of Japan, vol. 12, No. 467 (C-550) [3314], Dec. 7, 1988, & JP-A-63-185926, Aug. 1, 1988, T. Shigeru, et al., "Remedy for Hepatopathy".

Primary Examiner—Nicky Chan
Attorney, Agent, or Firm—Oblon, Spivak, McClelland, Maier & Neustadt

[57] ABSTRACT

Hepatopathy improvers contain as an effective ingredient one or more of benzodioxole derivatives represented by the following formula:

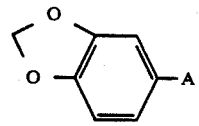

wherein A means a particular N- or S-containing group. Most of these benzodioxole derivatives are novel.

2 Claims, No Drawings

BENZODIOXOLE DERIVATIVES AND HEPATOPATHY IMPROVERS COMPRISING THE SAME

BACKGROUND OF THE INVENTION

1. Field of the Invention

This invention relates to benzodioxole, more specifically to benzodioxole derivatives having excellent hepatopathy improving effects and also to their preparation process and use.

2. Description of the Related Art

Hepatopathy caused by viral infection, overdrinking, fatigue or the like has increased in recent times, and indeed liver diseases are anticipated to become national diseases the 21st century.

To date, only an extremely small number of compounds are known to be effective for hepatopathy, and those used clinically are limited to just a very few.

These drugs are, however, not fully satisfactory because their GOT-value-improving effects are weak although they may be effective for the improvement of the GPT value.

The present assignee previously found that gomisin A isolated from schisandra fruit, crude drug, and represented by the following formula:

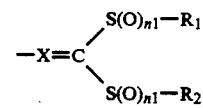

can promptly improve the GPT and GOT value of a hepatopath and is extremely useful as a hepatopathy improver. Subsequently, extensive research have been carried out to develop hepatopathy improvers based on gomisin A.

Gomisin A is, however, an extract from a natural raw material, so that its preparation steps are irksome and its yield is low. Further, the production of its raw material itself is limited. Gomisin A thus presents an economic problem in development as a drug.

It is therefore desirable to prepare gomisin A or a compound having similar drug efficacy thereto by chemical synthesis.

SUMMARY OF THE INVENTION

The present inventors conducted an investigation to determine the active center of gomisin A. Based on the results, various compounds having the active center have been synthesized and their pharmacological effects have been studied. As a result, it has been found that benzodioxole derivatives represented by the following formula (I'):

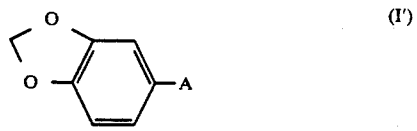

wherein A means a group represented by one of the following formulas:

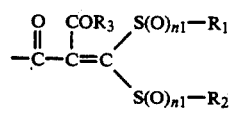

wherein X means $-CR_7=$ ($R_7$: a carboxyl or lower alkoxycarbonyl group), $-N=$ or $-N^+R'_8.X'^-=$ ($R_8$: a hydrogen atom or a lower alkyl, acyl or lower alkoxycarbonyl group, $X'^-$, $Cl^-$, $Br^-$, $I^-$, $H_2PO_4^-$, $HSO_4^-$, fumaric acid residue, acetic acid residue or maleic acid residue, $R_1$ and $R_2$ individually denote a lower alkyl group or are coupled together to form a $C_{1-3}$ alkylene group or $-CH=CH-$, and $n_1$ stands for an integer of 0–2;

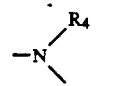

wherein $R_3$ means a hydroxyl, lower alkoxyl or substituted or unsubstituted amino group, and $R_1$, $R_2$ and $n_1$ have the same meanings as defined above;

wherein Y means a single bond, $-CO-$ or $-CS-$, $R_4$ denotes a hydrogen atom or a lower alkyl or lower alkoxycarbonylalkyl group, and $R'_5$ represents an alkylthio, carboxyl group or a group derived therefrom, an amino group or a group derived therefrom or an unsubstituted or lower alkylthio- or lower alkoxycarbonyl-substituted alkyl group, or $R_4$ and $YR'_5$ are coupled together to form $-CSSCOCH_2-$; and $-SR_6$ $R_6$ means a carboxyl group or a group derived therefrom, an amino group or a group derived therefrom, or an unsubstituted or lower alkylthio-substituted alkyl group, most of which are novel, have low toxicity and extremely strong hepatopathy improving effects, leading to the completion of this invention.

An object of this invention is therefore to provide hepatopathy improvers comprising as effective ingredients benzodioxole derivatives represented by the formula (I').

Another object of this invention is to provide novel benzodioxole derivatives (I).

The benzodioxole derivatives (I) of this invention can be classified into the following groups and can each be prepared by any one of processes to be described below.

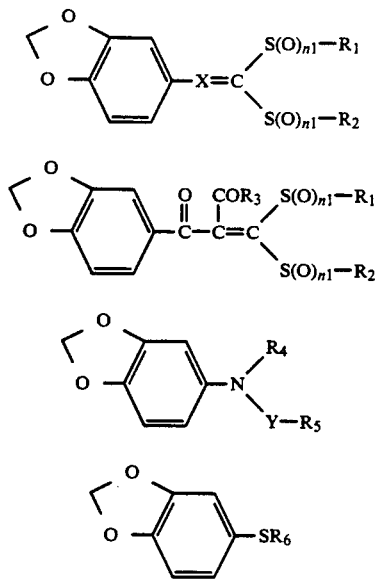

Preparation Process 1

(A) Of the compounds represented by the formula (Ia), the compounds in which X is —CR$_7$=, R$_1$ and R$_2$ are lower alkyl groups and n$_1$ is 0 [Compounds (Ia-1)] can each be prepared in accordance with the following reaction formula, i.e., by causing carbon disulfide and a lower alkylhalide (IIIa) to act on a 3,4-methylenedioxyphenylacetate ester represented by the formula (IIa) in the presence of an alkali and, if necessary, removing the ester group contained in the reaction product.

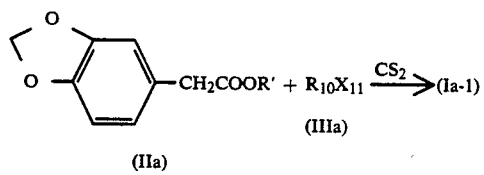

wherein R' and R$_{10}$ individually mean a lower alkyl group, and X$_{11}$ denotes a halogen atom.

The above reaction can be practiced in the presence of an alkali such as NaH, NaNH$_2$, t-BuOK, NaOH or KOH in a solvent, for example, tetrahydrofuran (THF), ethyl ether, dioxane or dimethylsulfoxide (DMSO). Illustrative halogens of the lower alkyl halide include Cl, Br and I.

The removal of the ester group can be conducted by hydrolyzing the reaction product in a manner known per se in the art. It is preferable to conduct this hydrolysis in the presence of an alkali such as NaOH or KOH in a solvent such as a lower alcohol or water.

(B) Of the compounds represented by the formula (Ia), the compounds in which X is —CR$_7$= or —N=, n$_1$ is 0 and R$_1$ and R$_2$ are coupled together to form a C$_{1-3}$ alkylene group [Compounds (Ia-2)] can each be prepared in accordance with the following reaction formula, i.e., by causing carbon disulfide and a compound represented by the formula (IIIb) to act on a 3,4-methylenedioxyphenylacetate ester or 3,4-methylenedioxyaniline (IIb) and, if necessary, removing the ester group contained in the reaction product.

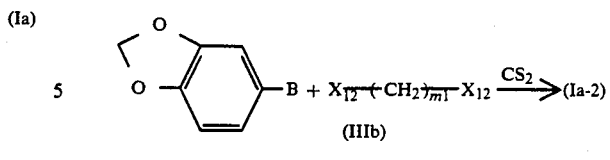

wherein B means —CH$_2$COOR' or —NH$_2$, R' having the same meaning as defined above, X$_{12}$ denotes a halogen atom and m$_1$ stands for an integer of 1-3.

The reaction can be conducted practically as in (A). Examples of the halogen atom in the compound (IIIb) include Cl, Br and I.

(C) Of the compounds represented by the formula (Ia), the compounds in which X is —CR$_7$= or —N=, n$_1$ is 0 and R$_1$ and R$_2$ are coupled together to form —CH=CH— [Compounds (Ia-3)] can each be prepared in accordance with the following reaction formula, i.e., by causing a 2-alkylthio-1,3-dithiolium salt represented by the formula (IIIc) to act on a 3,4-methylenedioxyphenylacetate ester or 3,4-methylenedioxyaniline (IIb) and, if necessary, removing the ester group contained in the reaction product.

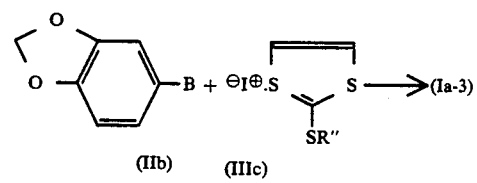

wherein R'' means a lower alkyl group and B has the same meaning as defined above.

This reaction can be conducted under reflux in the presence of an alkali such as NaH in a solvent such as tetrahydrofuran.

(D) Of the compounds represented by the formula (Ia), the compounds in which X is —CR$_7$= or —N= and n$_1$ is 1 or 2 [Compounds (Ia-4)] can each be prepared in accordance with the following reaction formula, i.e., by causing an inorganic or organic peroxide to act on the compound obtained by one of the above reactions (A)–(C) and represented by the formula (IId).

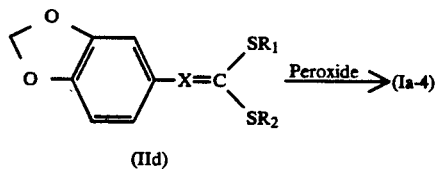

wherein R$_1$ and R$_2$ have the same meanings as defined above.

Illustrative inorganic peroxides usable in the above reaction include hydrogen peroxide and oxone, while examples of organic peroxides usable in the reaction include t-BuO$_2$H an dmCPBA. The reaction can be carried out in a solvent such as dichloromethane, chloroform, carbon tetrachloride, benzene, methanol, ethanol or acetone.

(E) Of the compounds represented by the formula (Ia), the compounds in which X is —N+R$_8$.X'−= [Compound (Ia-5)] can each be obtained in accordance with the following reaction formula, i.e., by causing a quaternizating agent represented by the formula (IIIe) to act on a compound (IIe), in which X is —N=, out of the compounds obtained by the above reactions (B)-(D).

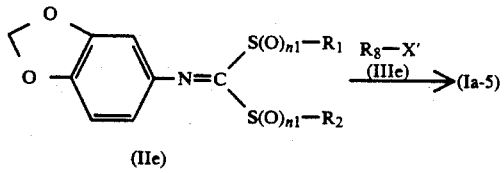

wherein $R_1$, $R_2$, $R_8$, $n_1$ and $X'$ have the same meanings as defined above.

This reaction can be conducted in a solvent such as THF, DMSO, DMF or acetone. Illustrative usable quaternizating agents include inorganic acids, organic acids, alkyl halides, acyl halides and acid anhydrides.

Preparation Process 2

(A) Of the compounds represented by the formula (Ib), the compounds in which $R_1$ and $R_2$ are lower alkyl groups, $R_3$ is a hydroxy group or a lower alkoxy group and $n_1$ is O [Compound (Ib-1)] can each be prepared in accordance with the following reaction formula, i.e., by causing carbon disulfide and a lower alkyl halide (Va) to act on a 3,4-methylenedioxyphenyl-3-oxopropionate ester represented by the formula (IVa) and, if necessary, removing the ester group contained in the reaction product.

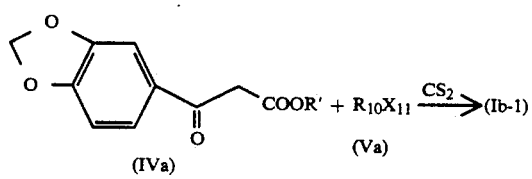

wherein R' means a lower alkyl group, and $R_{10}$ and $X_{11}$ have the same meanings as defined above.

This reaction can be practiced in the presence of an alkali such as NaH, NaNH$_2$, t-BuOK, NaOH or KOH in a solvent, for example, tetrahydrofuran (THF), ethyl ether, dioxane or dimethylsufoxide (DMSO). Examples of the halogen of the lower alkyl halide include Cl, Br and I.

The removal of the ester group can be conducted by hydrolyzing the reaction product in a manner known per se in the art. It is preferable to conduct this hydrolysis in the presence of an alkali such as NaOH or KOH in a solvent such as a lower alcohol or water.

(B) Of the compounds represented by the formula (Ib), the compounds in which $R_1$ and $R_2$ are coupled together to form a $C_{1-3}$ alkylene group, $R_3$ is a hydroxy group or a lower alkoxy group and $n_1$ is O [Compound (Ib-2)] can each be prepared in accordance with the following reaction formula, i.e., by causing carbon disulfide and a compound represented by the formula (Vb) to act on a 3,4-methylenedioxyphenyl-3-oxopropionate ester (IVa) in the presence of an alkali and, if necessary, removing the ester group contained in the reaction product.

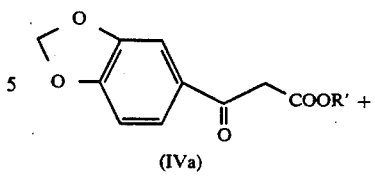

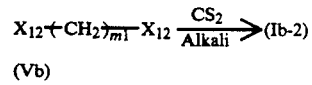

wherein $m_1$ means an integer of 1-3, and R' and $X_{12}$ have the same meanings as defined above.

The reaction can be conducted practically in a similar manner to (A). Examples of the halogen atom in the compound (Vb) include Cl, Br and I.

(C) Of the compounds represented by the formula (Ib), the compounds in which $R_1$ and $R_2$ are coupled together to form —CH=CH—, $R_3$ is a hydroxy group or a lower alkoxy group and $n_1$ is O [Compound (Ib-3)] can each be prepared in accordance with the following reaction formula, i.e., by causing a 2-alkylthio-1,3-dithiolium salt represented by the formula (Vc) to act on a 3,4-methylenedioxyphenyl-3-oxopropionate ester (IVa) and, if necessary, removing the ester group contained in the reaction product. The removal of the ester group can be effected in a similar manner to the hydrolysis described above in (A).

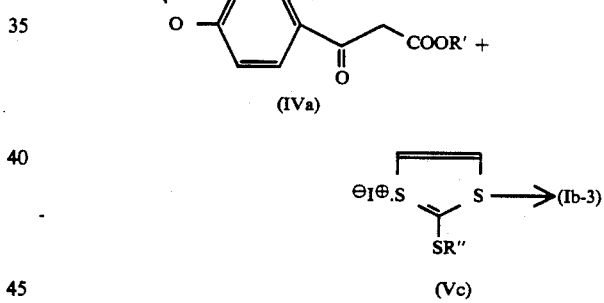

wherein R' and R'' have the same meanings as defined above.

This reaction can be conducted under reflux in the presence of an alkali such as NaH in a solvent such as tetrahydrofuran.

(D) Of the compounds represented by the formula (Ib), the compounds in which $R_1$ and $R_2$ are coupled together to form —CH=CH—, $n_1$ is O and $R_3$ is a substituted or unsubstituted amino group [Compound (Ib-3')] can each be prepared in accordance with the following reaction formula, i.e., by causing an amine represented by the formula (Vd) to act on a carbonic acid (Ib-3''), in which $R_3$ is a hydroxyl group, out of the compounds (Ib-3).

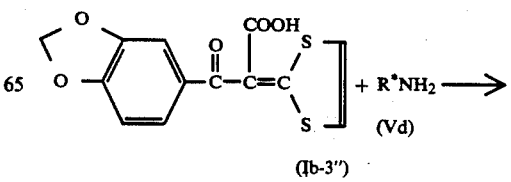

-continued

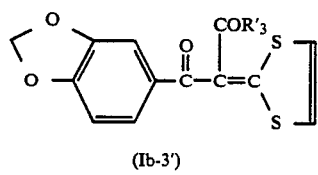

(Ib-3')

wherein R* is a substituted or unsubstituted alkyl group, and R'$_3$ is a substituted or unsubstituted amino group.

This reaction can be conducted in the presence of an alkali such as Et$_3$N, DIEA, Me$_3$N or NaH in a solvent such as DMF or DMSO, using a condensing agent such as DCC, DPPA or DEPC.

(E) Of the compounds represented by the formula (Ib), the compounds in which n$_1$ is 1 or 2 [Compound (Ib-4)] can each be obtained in accordance with the following reaction formula, i.e., by causing an inorganic or organic peroxide to act on one of the compounds obtained in the above reactions (A)–(D) and represented by the formula (IVe).

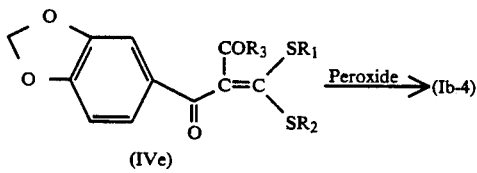

(IVe)

wherein R$_1$, R$_2$ and R$_3$ have the same meanings as defined above.

Illustrative inorganic peroxides usable in the above reaction include hydrogen peroxide and oxone, while examples of organic peroxides usable in the reaction include t-BuO$_2$H and mCPBA. The reaction can be carried out in a solvent such as dichloromethane, chloroform, carbon tetrachloride, benzene, methanol, ethanol or acetone.

Preparation Process 3

(A) Of the compounds represented by the formula (Ic), the compounds in which Y is —CS—, R$_4$ is a lower alkoxycarbonylalkyl group and R$_5$ is a lower alkylthio group [Compounds (Ic-1)] can each be obtained in accordance with the following formula, i.e., by causing the compound represented by the formula (VIIa) to act on the compound represented by the formula (VIa).

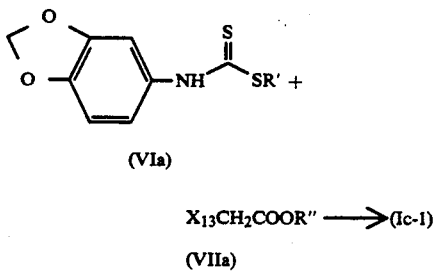

(VIa)

$X_{13}CH_2COOR'' \longrightarrow$ (Ic-1)

(VIIa)

wherein R' and R'' have the same meanings as defined above, and X$_{13}$ means a halogen atom or a tosyloxy or mesyloxy group.

The above reaction can be practiced in the presence of an alkali, e.g., KH, NaH, NaNH$_2$ or n-BuLi in a solvent such as THF, DME, diglyme, ethyl ether, DMF or DMSO.

(B) Of the compounds represented by the formula (Ic), the compounds in which Y is a single bond, R$_4$ is a hydrogen atom and R$_5$ is a lower alkoxycarbonylalkyl group [Compounds (Ic-2)] can each be obtained in accordance with the following formula, i.e., by causing the compound represented by the formula (VIIb) to act on 3,4-methylenedioxyaniline represented by the formula (VIb).

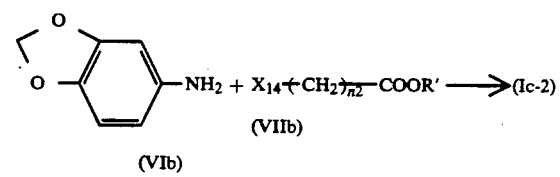

(VIb)

wherein X$_{14}$ means a halogen atom or a tosyloxy or mesyloxy, n$_2$ denotes an integer of 1-5, and R' has the same meaning as defined above.

The above reaction can be practiced in the presence of an alkali, e.g., KOH, NaOH, KH, NaH or t-BuOK in a solvent such as THF, DME, diglyme, ethyl ether, DMF, DMSO, benzene or toluene.

(C) Of the compounds represented by the formula (Ic), the compounds in which Y is —CO—, R$_4$ is a hydrogen atom or a lower alkyl or lower alkoxycarbonylalkyl group and R$_5$ is a carboxyl group or a group derived therefrom, an amino group or a group derived therefrom or an unsubstituted or lower alkylthio-substituted alkyl group [Compounds (Ic-3)] can each be obtained in accordance with the following formula, i.e., by condensing a carboxylic acid represented by the formula (VIIc) with 3,4-methylenedioxyaniline or a derivative thereof, represented by the formula (VIc), and, if necessary, removing any protecting group contained in the reaction product.

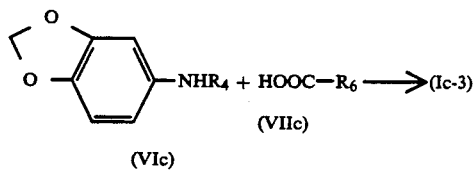

(VIc)

wherein R$_4$ and R$_6$ have the same meanings as defined above.

The above condensation can be practiced by a known peptide synthesis process. For example, at 0° C. to room temperature, 3,4-methylenedioxyaniline or its derivative (VIc) and the carboxylic acid (VIIc) can be condensed by using a dehydrating condensing agent such as dicyclohexylcarbodiimide (DCC). As an alternative, it is also possible to conduct the condensation by causing, for example, a halogenated carbonate ester such as methyl chloroformate, ethyl chloroformate or isobutyl chloroformate or an acyl halide such as isobutyryl chloride or 2,6-dichlorobenzoyl chloride to act on the carboxylic acid (VIIc) to convert the latter to its acid anhydride and then reacting 3,4-methylenedioxyaniline or its derivative (VIc) on the acid anhydride in the presence of a base such as triethylamine. These reactions can be conducted in a solvent such as a halogenated hydrocarbon or an ether.

The removal of the protecting group from the reaction product can be effected at room temperature. Illustrative acids usable therefor include hydrochloric acid, sulfuric acid and trifluoroacetic acid.

Examples of protecting groups for the amino and carboxyl groups in the compound (VIIc) include BOC, Cbz and lower alkyl groups. L-cystein can be mentioned as one example of the carboxylic acid compound (VIIc).

(D) Of the compounds represented by the formula (Ic), the compounds in which R$_4$ and YR$_5$ are coupled together to form —CSSCOCH$_2$— [Compounds (Ic-4)] can each be obtained by causing carbon disulfide to act on the compound represented by the formula (VId).

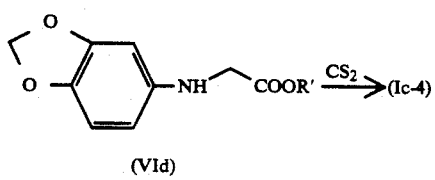

(VId)

wherein R' has the same meaning as defined above.

The above reaction can be conducted in a solvent such as THF, DME, diglyme, ethyl ether, DMF, DMSO, benzene or toluene. Examples of the alkali include KOH, NaOH, KH and NaH.

(E) Of the compounds represented by the formula (Ic), the compounds in which Y is —CS—, R$_4$ is a hydrogen atom, a lower alkyl or a lower alkoxycarbonylalkyl group, and R$_5$ is a carboxyl group or a group derived therefrom, an amino group or a group derived therefrom or an unsubstituted or lower alkylthio-substituted alkyl group [Compounds (Ic-5)] can each be obtained in accordance with the following reaction formula, i.e., by causing P$_2$S$_5$ to act on a 3,4-methylenedioxyaniline derivative represented by the formula (VIe) and, if necessary, removing any protecting group contained in the reaction product.

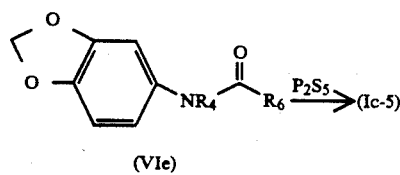

(VIe)

wherein R$_4$ and R$_6$ have the same meanings as defined above.

The reaction in which P$_2$S$_5$ is caused to act on the compound (VIe) can be conducted under reflux in a hydrocarbon solvent. Further, the removal of the protecting group can be effected by causing hydrochloric acid, sulfuric acid or trifluoroacetic acid to act at room temperature or so in a hydrocarbon, acetate ester or ether solvent.

(F) Of the compounds represented by the formula (Ic), the compounds in which Y is a single bond, R$_4$ is a hydrogen atom, a lower alkyl or a lower alkoxycarbonylalkyl group and R$_5$ is a carboxyl group or a group derived therefrom, an amino group or a group derived therefrom or an unsubstituted or lower alkylthio-substituted alkyl group [Compounds (Ic-5)] can each be obtained in accordance with the following reaction formula, i.e., by reducing a 3,4-methylenedioxyaniline derivative represented by the formula (VIe) and, if necessary, removing any protecting group contained in the reaction product.

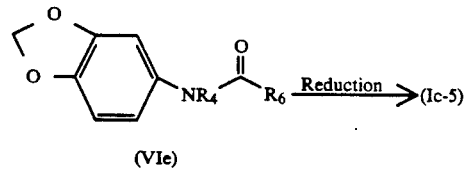

(VIe)

wherein R$_4$ and R$_6$ have the same meanings as defined above.

The above reducing reaction can be conducted at room temperature in a solvent such as THF, ethyl ether, DMF, benzene, toluene, methanol or ethanol. Illustrative usable reducing agents include B$_2$H$_6$, (iBu)$_2$AlH, Li/EtNH$_2$, NaBH$_4$/AcOH, NaBH$_4$/CoCl$_2$, PCl$_5$/NaBH$_4$, LiAlH$_4$, BH$_3$.Me$_2$S and BH$_3$.THF. The removal of the protecting group can be practiced in a similar manner to (E).

Preparation Process 4

The compounds represented by the formula (Id) can each be obtained in accordance with the following reaction formula, i.e., by causing a compound represented by the formula (IX) to act on 3,4-methylenedioxymercaptan represented by the formula (VIII).

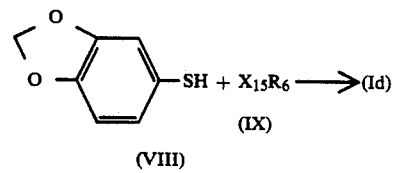

(VIII)

wherein X$_{15}$ means atom or a tosyloxy group, and R$_6$ has the same meaning as defined above.

The above reaction can be conducted at room temperature or so in the presence of an alkali, e.g., KH, NaH, t-BuOK, K$_2$CO$_3$, Na$_2$CO$_3$, KOH or NaOH in a solvent such as THF, dioxane, DMF, diglyme, DMSO, benzene or toluene.

The benzodioxole derivatives (I) of this invention, which have been obtained as described above, can be collected from reaction mixtures by a known purification technique such as recrystallization or column chromatography.

The benzodioxole derivatives (I) of this invention can be converted to inorganic acid salts, organic acid salts or the like as needed. Such inorganic acid salts or organic acid salts include pharmacologically-acceptable salts with inorganic acids or organic acids.

Pharmacological activities of the benzodioxole derivatives (I') according to this invention were tested. The results will next be described.

(1) Hepatopathy improving effects

The hepatopathy improving effects of the compounds (I') of this invention for CCl$_4$-induced hepatopath rats were investigated by using, as an index, the inhibition to the increase of transaminase in serum. After SD male rats (7 weeks old; Japanese Charles River) had been fasted for 24 hours, test drugs were orally administered at 100 mg/kg. Thirty minutes later, a CCl$_4$ solution (diluted fourfold with olive oil) was peritoneally administered at 4 mg/kg. The rats were fasted further for 24 hours and then anesthetized with 1 ml/kg of sodium pentobarbital. After a blood sample was collected from the descending abdominal aorta of each rat, the liver was enucleated and its wet weight was measured. Further, the GOT and GPT of a serum, which had been obtained from the blood sample so collected, were measured by an automatic chemical analyzer ("TBA-380", trade name; manufactured by Toshiba Corp.). Thick serums were measured after dilution in distilled water.

The results are summarized in Table 1.

TABLE 1

| Test compound | Serum GOT (U/l) | Serum GPT (U/l) |
|---|---|---|
| Example 1 | 432 | 74 |
| Example 2 | 563 | 100 |
| Example 3 | 2573 | 557 |
| Example 5 | 391 | 57 |
| Synthesis Example 1 | 1027 | 230 |
| Synthesis Example 2 | 1400 | 310 |
| Control 1 | 89 | 20 |
| Control 2 | 7719 | 1071 |

Note: Control 1 is a group not administered with $CCl_4$ while Control 2 is a group administered with $CCl_4$ alone.

(2) Acute toxicity

Using ICR male rats, acute toxicity was tested by oral administration. As a result, no case of death was observed even when the compounds (I') of this invention were administered at 1000 mg/kg.

(3) Mutagenicity test

Using two types of strains, Salmonella TA98 and TA100, mutagenecity was tested by the Ames method. As a result, no mutagenecity was observed.

As has been demonstrated above, the benzodioxole derivatives (I') of this invention have low toxicity and extremely strong hepatopathy improving effects. They can therefore be used as hepatopathy improvers.

To formulate hepatopathy improvers by using the benzodioxole derivatives (I') of this invention, it is only necessary to formulate the benzodioxole derivatives (I') together with a known pharmaceutical carrier into dosable preparations by a method known per se in the art.

No particular limitation is imposed on the manner of administration of the hepatopathy improvers according to this invention. They can be administered either as an oral preparation such as tablets, capsules, granules, fine granules, powder or solution or as a parenteral preparation such as injection or drip infusion.

A suitable pharmaceutical carrier can be chosen depending on the manner of administration or the preparation form. For oral preparations, starch, lactose, sucrose, mannitol, carboxymethylcellulose, corn starch, inorganic salts or the like can be used. Upon formulation of parenteral preparations, one or more of binders, disintegrators, surfactants, lubricants, fluidity improvers, corrigents, colorants, perfumes and the like can also be added. The followings are their specific examples.

Binders

Starch, dextrin, gum arabic powder, gelatin, hydroxypropyl starch, methylcellulose, sodium carboxymethylcellulose, hydroxypropylcellulose, crystalline cellulose, ethylcellulose, polyvinylpyrrolidone, and macrogol.

Disintegrators

Starch, hydroxypropyl starch, sodium carboxymethylcellulose, calcium carboxymethylcellulose, carboxymethylcellulose, and low-substituted hyroxypropylcellulose.

Surfactants

Sodium laurylsulfate, soybean lecithin, sucrose fatty acid esters, and polysolbate 80.

Lubricants

Talc, waxes, hydrogenated vegetable oils, sucrose fatty acid esters, magnesium stearate, calcium stearate, aluminum stearate, and polyethylene glycol.

Fluidity improvers

Light anhydrous silicic acid, dried aluminum hydroxide gel, synthetic aluminum silicate, and magnesium silicate.

Illustrative oral solutions include suspensions, emulsions, syrups and elixirs. These preparations can be added with one or more of corrigents and colorants.

Further, peritoneal preparations can be formulated by either dissolving or suspending the effective ingredients of this invention in injection-grade distilled water, physiological saline, aqueous glucose solution, injection-grade vegetable oil, sesame oil, peanut oil, soybean oil, corn oil, propylene glycol or polyethylene glycol as a diluent in a manner known per se in the art and, if necessary, adding one or more of fungicides, antiseptics, stabilizers, isotonicities, soothing agents and the like.

The dosage of the hepatopathy improvers of the present invention varies depending on the administration route, the severity of disease, the age of each patient, etc. In general, the hepatopathy improvers can be administered at a daily dosage of 5-500 mg or so per adult in terms of the benzodioxole derivatives (I') in 1-3 portions.

The benzodioxole derivatives (I') according to this invention can be obtained by chemical synthesis and have excellent hepatopathy improving effects, for example, lower GOT and GPT values. They are hence extremely useful as hepatopathy improvers.

The present invention will next be described in further detail. It is, however, to be borne in mind that the present invention shall not be limited to or by the following examples.

EXAMPLE 1

Synthesis of
N,N-(1,3-dithiol-2-ylidene)-1,3-benzodioxol-5-amine

In 40 ml of tetrahydrofuran, 2.33 g of 3,4-(methylenedioxy)aniline and 4.94 g of 2-methylthio-1,3-dithiolium iodide were suspended. The suspension was refluxed for one hour. The reaction mixture was added with triethylamine, followed by stirring for a while. The solvent was distilled off to obtain a residue. The residue was purified by column chromatography (silica gel: "MERCK 9385", 1.21 kg, column: 100 mm across×363 mm long, $N_2$ pressure: 0.2 kg/cm$^2$, developer: chloroform:n-hexane=3:1→4:1). The oil thus obtained was decolored by activated carbon (solvent: methanol) and then recrystallized from a chloroform-n-hexane mixed solvent, whereby 1.23 g of N,N-(1,3-dithiol-2-ylidene)-1,3-benzodioxol-5-amine were obtained as yellow needle crystals (yield: 30.5%).

Melting point: 92.0°–93.5° C.

IR (KBr)$\nu_{max}$ cm$^{-1}$: 1586, 1502, 1480, 1240, 1186, 1034, 928, 916, 816, 648.

$^1$H-NMR (CDCl$_3$) δ [200 MHz] ppm: 5.97(2H,s), 6.49(1H,d,J=7.6 Hz), 6.51(1H,dd, J=2.2,8.3 Hz), 6.57(1H,d,J=7.6 Hz), 6.59(1H,d, J=2.2 Hz), 6.80(1H,d,J=8.3 Hz).

MS m/z (%) [EI-MS]: 237 (100,M+), 179(29), 147(44), 146(50).

Elemental analysis (as C$_{10}$H$_7$O$_2$NS$_2$): Calculated (%): C, 50.62; H, 2.97; N, 5.90. Found (%): C, 50.64; H, 2.87; N, 5.90.

EXAMPLE 2

Synthesis of isopropyl 2-(1,3-dithiol-2-ylidene)-3-[3,4-(methylenedioxy)-phenyl]-3-oxopropionate

(1) Preparation of isopropyl 3-hydroxy-3-[3,4-(methylenedioxy)phenyl]propionate In 200 ml of dry benzene, 7.50 g of piperonal and 10.5 g of isopropyl bromoacetate were dissolved. To 30 ml of the resultant solution, 18.6 g of zinc powder was added, followed by stirring at 80° C. under an argon stream. At that time, the reaction mixture foamed. After the foaming subsided, the remaining benzene solution was gradually added dropwise and, after the dropwise addition, the resulting mixture was refluxed for three hours. The reaction mixture was ice-cooled and then added with a 10% aqueous solution of sulfuric acid, followed by stirring for one hour and subsequent extraction with ether. The organic layer thus obtained was washed with water, shaken together with a saturated aqueous NaCl solution and then dried over anhydrous magnesium sulfate. The solvent was distilled off, whereby yellow crude oil was obtained. The crude oil was purified by column chromatography, whereby 11.9 g of isopropyl 3-hydroxy[3,4-(methylenedioxy)phenyl]-propionate were obtained as pale yellow oil (yield 94.4%).

IR (NaCl)$\nu_{max}$ cm$^{-1}$: 3464, 2980, 1726, 1502, 1284, 1180, 1038. $^1$H-NMR (CDCl$_3$) δ [200 MHz] ppm: 1.24(6H,d,J=6.1 Hz), 3.28(1H,d,J=3.2 Hz), 5.06(1H, Sept.,J=6.1 Hz), 5.00–5.09(1H,m), 5.95(2H,s), 6.76 (1H,d,J=8.1 Hz), 6.83(1H,dd,J=1.7,8.1 Hz), 6.89(1H,d,J=1.7 Hz)

MS m/z (%) [EI-MS]: 252 (7,M+), 234(26), 192(32), 175(24), 149(100).

(2) Preparation of isopropyl 3-[3,4-methylenedioxy)phenyl]-3-oxopropionate

In 500 ml of chloroform, 25.8 g of the isopropyl 3-hydroxy-3-[3,4-(methylenedioxy)phenyl]propionate obtained above in (1) were dissolved, followed by the addition of 150 g of manganese dioxide. The resulting mixture was stirred for one day at room temperature. The reaction mixture was filtered, using Celite and then, the solvent of the filtrate was distilled off, whereby 27.8 g of yellow crude oil were obtained. The crude oil was purified by column chromatography (silica gel: "MERCK 9385", 1.59 g, column: 100 mm across×459 mm long, N$_2$ pressure 0.2 kg/cm$^2$, developer: ethyl acetate:n-hexane=1:8), whereby 21.1 g of isopropyl 3-[3,4-(methylenedioxy)phenyl]-3-oxopropionate were obtained as colorless oil (yield: 82.4%).

IR (NaCl)$\nu_{max}$ cm$^{-1}$: 2984, 1732, 1446, 1248, 1104.

$^1$H-NMR (CDCl$_3$) δ [200 MHz] ppm: 1.24(6H,d,J=6.4 Hz), 3.88(2H,s), 5.07(1H,Sept., J=6.4 Hz), 6.06(2H,s), 6.86(1H,d,J=8.3 Hz), 7.42 (1H,d,J=1.7 Hz), 7.52(1H,dd,J=1 7,8.3 Hz).

MS m/z (%) [EI-MS]: 250 (13,M+), 149(100).

(3) Preparation of isopropyl 2-(1,3-dithiol-2-ylidene)-3-[3,4-(methylenedioxy)-phenyl]-3-oxopropionate In 5 ml of tetrahydrofuran, 428 mg of sodium hydride were suspended. Under ice cooling, the suspension was added with 20 ml of a tetrahydrofuran solution of 2.68 g of the isopropyl 3-[3,4-(methylenedioxy)phenyl]-3-oxopropionate, which had been obtained above in (2), followed by stirring for a while. Further, the reaction mixture was added with 3.25 g of 2-methylthio-1,3-dithiolium iodide and then refluxed for three hours. The reaction mixture was poured into ice water, followed by extraction with ether. The organic layer was washed with water, shaken together with a saturated aqueous NaCl solution and then dried over anhydrous sodium sulfate. The solvent was distilled off, whereby 4.80 g of black crude crystals were obtained. The crude crystals were purified by column chromatography (crude crystal: 4.80 g, silica gel: MERCK 9385, 913 g, column: 100 mm across×261 mm long, N$_2$ pressure: 0.2 kg/cm$^2$, developer: ethyl acetate:n-hexane=2:5) and then recrystallized from a chloroform-n-hexane mixed solvent, whereby 3.00 g of isopropyl 2-(1,3-dithiol-2-ylidene)-3-[3,4-(methylenedioxy)phenyl]-3-oxopropionate were obtained (79.9%).

Melting point: 136.5°–137.5° C.

IR (KBr)$\nu_{max}$ cm$^{-1}$: 1666, 1570, 1402, 1356, 1266, 1256, 1106, 1034.

$^1$H-NMR (CDCl$_3$) δ [200 MHz] ppm: 1.01(6H,d,J=6.4Hz), 5.01(1H,Sept.,J=6.4Hz), 6.01 (2H,s), 6.80(1H,dd,J=1.0,7.8 Hz), 7.08–7.14(2H,m), 7.17(1H,d,J=6.6 Hz), 7.25(1H,d,J=6.6 Hz).

MS m/z (%) [EI-MS]: 350(100,M+), 264(94), 149(91).

Elemental analysis (as C$_{16}$H$_{14}$O$_5$S$_2$): Calculated (%): C, 54.84; H, 4.03. Found (%): C, 54.74; H, 3.95.

EXAMPLE 3

Synthesis of isopropyl 2-(1,3-dithiol-2-ylidene)-2-[3,4-(methylenedioxy)phenyl]acetate

(1) Synthesis of isopropyl (3,4-dihydroxyphenyl)acetate

In dry benzene, 20.0 g of 3,4-dihydroxyphenylacetic acid were dissolved. The solution was added with 2 ml of concentrated sulfuric acid and 200 ml of isopropyl alcohol. The resulting mixture was refluxed for 10 hours under an argon stream while being dried through molecular sieves. The reaction mixture was extracted with ether. The organic layer was washed with water, shaken together with a saturated aqueous NaCl solution and then dried over anhydrous sodium sulfate. The solvent was distilled off, whereby 32.5 g of black crude oil were obtained. The crude oil thus obtained was purified by column chromatography (crude oil: 32.5 g, silica gel: MERCK 9385, 615 g, column: 100 mm across×171 mm long, N$_2$ pressure 0.3 kg/cm$_2$, developer: chloroform:methanol=40:1), whereby 24.6 g of isopropyl (3,4-dihydroxyphenyl)acetate were obtained as colorless oil (yield: 98.4%).

IR (NaCl)$\nu_{max}$ cm$^{-1}$: 3380, 1708, 1522, 1448, 1374, 1286, 1194, 1148, 1104.

$^1$H-NMR (CDCl$_3$) δ [200 MHz] ppm: 1.24(6H,d,J=6.4 Hz), 3.46(2H,s), 5.02(1H,Sept., J=6.4

Hz), 6.62(1H,d,J=2.0,8.1 Hz), 6.72(1H,d, J=8.1 Hz), 6.73(1H,d,J=2.0 Hz).

MS m/z (%) [EI-MS]: 210 (24,M+), 166(17), 123(100).

High-MS m/z (%) [EI-MS]: Calculated for $C_{11}H_{14}O_4$ (M+): 210.08927. Found: 210.09127.

(2) Synthesis of isopropyl [3,4-(methylenedioxy)phenyl]acetate

Dissolved in 450 ml of dry N,N-dimethylformamide were 24.3 g of the isopropyl (3,4-dihydroxyphenyl)acetate obtained above in (1). To the solution, 33.5 g of potassium carbonate and 10.2 ml of diiodomethane were added, followed by stirring at 100° C. under an argon stream for 4 hours. The reaction mixture was filtered and the solvent of the filtrate was distilled off, whereby black crude oil was obtained as a residue. The residue was purified by column chromatography (silica gel: MERCK 9385, 560 g, column: 100 mm across×158 mm long, $N_2$ pressure: 0.3 kg/cm², developer: chloroform: n-hexane=1:1), whereby 16.9 g of isopropyl [3,4-(methylenedioxy)phenyl]acetate were obtained as pale yellow oil (yield: 65.8%).

IR (NaCl)$\nu_{max}$ cm$^{-1}$: 1728, 1502, 1492, 1446, 1246, 1182, 1144, 1106, 1038, 930.

$^1$H-NMR (CDCl$_3$) δ [200 MHz] ppm: 1.23(6H,d,J=6.4 Hz), 3.48(2H,s), 5.00(1H,Sept., J=6.4 Hz), 5.93(2H,s), 6.72-6.79(3H,m).

MS m/z (%) [EI-MS]: 222 (30,M+), 135(100).

High-MS m/z (%) [EI-MS]: Calculated for $C_{12}H_{14}O_4$ (M+): 222.08929. Found: 222.08949.

(3) Synthesis of isopropyl 2-(1,3-dithiol-2-ylidene)-2-[3,4-(methylenedioxy)phenyl]acetate Dissolved in 100 ml of dry tetrahydrofuran were 6.51 g of isopropyl [3,4-(methylenedioxy)phenyl]acetate obtained above in (2). Under an argon stream, the resultant solution was ice-cooled, added with 2.34 g of sodium hydride and then stirred for a while. 2-Methylthio-1,3-dithiolium iodide (8.09 g) was added, followed by refluxing for 40 minutes. An aqueous solution of ammonium chloride was added to the reaction mixture, followed by extraction with chloroform. The organic layer was washed with water, shaken together with a saturated aqueous NaCl solution and then dried over anhydrous sodium sulfate. The solvent was distilled off, whereby black oil was obtained as a residue. The residue was purified by column chromatography (silica gel: MERCK 9385, 1.13 kg, column: 100 mm across×329 mm long, $N_2$ pressure: 0.3 kg/cm², developer: ethyl acetate:n-hexane=1:8) and then recrystallized from a chloroform-n-hexane mixed solvent, whereby 3.45 g of isopropyl 2-(1,3-dithiol-2-ylidene)-2-[3,4-(methylenedioxy)phenyl]acetate were obtained as orange plate crystals (yield: 36.5%).

Melting point: 145°-146° C.

IR (KBr)$\nu_{max}$ cm$^{-1}$: 1646, 1504, 1472, 1300, 1256, 1238, 1208, 1102, 1036.

$^1$H-NMR (CDCl$_3$) δ [200 MHz] ppm: 1.20(6H,d,J=6.4 Hz), 5.08(1H,Sept ,J=6.4 Hz), 6.00(2H,s), 6.48(1H,d,J=6.6 Hz), 6.72(1H,d, J=6.6 Hz), 6.72-6.77(2H,m), 6.85(1H,dd, J=7.6,0.7 Hz).

MS m/z (%) [EI-MS]: 323(14), 322(55,M+), 281(23), 280(100).

Elemental analysis (as $C_{15}H_{14}O_4S_2$): Calculated (%): C, 55.88; H, 4.38. Found(%): C, 55.75; H, 4.12.

EXAMPLE 4

Synthesis of methyl [S-(3,4-methylenedioxy)phenyl]cysteinate hydrochloride (A) After 27.7 g of (3,4-methylenedioxy)thiophenol and 74 g of methyl N-(t-butoxycarbonyl)-O-tosyl-L-serinate were dissolved in 200 ml of chloroform, 20 g of triethylamine were added at room temperature, followed by stirring overnight. The reaction mixture was washed with water and then extracted with ethyl acetate. The extract so obtained was dried over anhydrous magnesium sulfate. After the solvent was distilled off, 49 g of crude oil were obtained. The crude oil was recrystallized from an ethyl acetatehexane system, whereby 42 g of methyl N-t-butoxycarbonyl-S-[(3,4-methylenedioxy)phenyl]cysteinate were obtained (yield: 66%).

(B) After 40 g of the methyl N-t-butoxycarbonyl-S-[(3,4-methylenedioxy)phenyl]-cysteinate obtained above in (A) were dissolved in 500 ml of ethyl acetate, hydrochloric acid gas was ebulated at room temperature under stirring until no fresh precipitate was formed. The colorless precipitate so obtained was collected by filtration and then dried, whereby 27.8 g of methyl [S-(3,4-methylenedioxy)phenyl]cysteinate hydrochloride were obtained (yield: 85%).

IR (KBr)$\nu_{max}$ cm$^{-1}$: 3028, 2896, 2828, 2672, 2620, 1748, 1576, 1506, 1474, 1440, 1416, 1338, 1324, 1274, 1240, 1124, 1104, 1076, 1034, 928, 888, 806.

$^1$H-NMR (CD$_3$OD) δ [200 MHz] ppm: 3.399(2H,d,J=5.5 Hz), 3.618(3H,s), 4.155(1H,dd, J=5.5,5.5 Hz), 4.848(3H,s), 5.989(2H,s), 6.815(1H, dd,J=6.5,2 Hz), 7.05(1H,s), 7.073(1H,dd,J=6.5,2 Hz).

MS m/z (%) [FAB]: 256(M+-Cl), 185, 153.

EXAMPLE 5

Synthesis of [3,4-methylenedioxy)aniline]-S-methylcysteinamide hydrochloride (A) In 20 ml of chloroform, 1.37 g of N-t-butoxycarbonyl-S-methyl-cysteine were dissolved. After the solution was cooled to 0° C., 1.1 g of triethylamine were added. Isopropyl chloroformate (1.5 g) was then added, followed by stirring for 15 minutes. At the same temperature, 1.37 g of 3,4-methylenedioxyaniline were added. The temperature of the resultant mixture was allowed to rise to room temperature, at which the mixture was stirred for 5 hours. The reaction mixture was washed with water and then extracted with ethyl acetate. The extract so obtained was dried over anhydrous magnesium sulfate. After the solvent was distilled off, 2.8 g of brown syrup were obtained. The crude substance was subjected to flash column chromatography, whereby 2.3 g of [(3,4-methylenedioxy)aniline]-N-t-butoxycarbonyl-S-methylcysteinamide were obtained as substantially colorless powder (yield: 65%).

IR (KBr)$\nu_{max}$ cm$^{-1}$: 3324, 3112, 2980, 2924, 1680, 1662, 1640, 1616, 1566, 1522, 1504, 1492, 1450, 1416, 1392, 1370, 1342, 1326, 1292, 1274, 1256, 1216, 1184, 1164, 1102, 1036, 1000, 954, 928, 876, 864, 810, 782, 716, 642, 614.

$^1$H-NMR (CDCl$_3$) δ [200 MHz] ppm: 1.472(9H,s), 2.171(3H,s), 2.885(1H,dd, J=14.7 Hz), 2.977(1H,dd,J=14.6 Hz), 4.353(1H,dd, J=7,6 Hz), 5.473(1H,d,J=7 Hz), 5.944(2H,s), 6.733(1H,d,J=8 Hz), 6.820(1H,dd,J=8.2 Hz), 7.216(1H,d,J=2 Hz), 8.314(1H,d).

(B) After 1.83 g of the [(3,4-methylenedioxy)aniline]-N-t-butoxycarbonyl-S-methylcysteinamide obtained above in (A) were dissolved in 20 ml of ethyl acetate, hydrochloric acid gas was ebulated at room temperature under stirring until no fresh precipitate was formed. The colorless precipitate so obtained was collected by filtration and then dried, whereby 1.25 g of [(3,4-methylenedioxy)aniline]-S-methylcysteinamide hydrochloride were obtained (yield: 83%).

IR (KBr)$\nu_{max}$ cm$^{-1}$: 3436, 3224, 3072, 2900, 1690, 1640, 1620, 1574, 1490, 1454, 1346, 1286, 1242, 1186, 1124, 1100, 1036, 926, 810, 606.

$^1$H-NMR (D$_2$O) δ [200 MHz] ppm: 2.110(3H,s), 3.107(1H,dd,J=15,7 Hz), 3.402(1H,dd,J=15,7 Hz), 4.379(1H,dd,J=7 Hz), 6.016(3H,s), 6.899(1H,dd,J=8.5,1.5 Hz), 6.952(1H,d,J=8.5 Hz), 7.115(d,J=1.5 Hz).

MS m/z (%) [FAB]: 255(M+-Cl), 190, 137, 115.

EXAMPLE 6

Synthesis of isopropyl 2-(1,3-dithiol-2-ylidene)-3-[3,4-(methylenedioxy)-phenyl]-3-oxopropionate Isopropyl 3-(1,3-benzodioxol-5-yl)-3-oxopropionate (2.5 g) was dissolved in 30 ml of DMSO, to which 2.2 ml of 10N potassium hydroxide and 0.7 ml of carbon disulfide were added under ice cooling. The temperature of the resulting mixture was allowed to rise to room temperature, at which the mixture was stirred for 1 hour. The reaction mixture then turned to a reddish clear solution. After the reaction mixture was ice-cooled again, 1.066 g of cis-1,2-dichloroethylene were added, the temperature of the resultant mixture was allowed to rise to room temperature, followed by stirring for 3 hours. When the solution was poured into ice water, crystals precipitated. Those crude crystals were recrystallized from benzene-hexane, whereby 385 mg of isopropyl 2-(1,3-dithiol-2-ylidene)-3-[3,4-(methylenedioxy)phenyl]-3-oxopropionate were obtained as reddish crystals (yield: 11%).

$^1$H-NMR (CDCl$_3$): 1.040(6H,d,J=6.5 Hz), 5.0–5.2(1H,m), 6.004(2H,s), 6.793(1H,d,J=8 Hz), 7.135(1H,dd,J=2,1Hz), 7.178(1H,d,J=1Hz), 7 199(1H,dd,J=8,1Hz), 7.258(1H,d,J=2 Hz).

EXAMPLE 7

Synthesis of (N-methyl-1,3-benzodioxol-5-ylamino)-N-t-butoxycarbonyl-S-methyl-L-cysteinamide In 10 ml of chloroform, 5.875 g (25 mmol) of N-t-butoxycarbonyl-S-methyl-L-cysteine were dissolved, followed by the successive addition of 2.778 g (27.5 mmol) of triethylamine and 3.756 g 27.5 mmol) of isobutyl chloroformate under ice cooling. The mixture so obtained was stirred for 15 minutes. The reaction mixture was then added under ice cooling with 3.775 g (25 mmol) of N-methyl-1,3-methylenedioxyaniline. The mixture was gradually heated and was stirred overnight at room temperature. The solution was added with 300 ml of ethyl acetate, washed with water and then dried over anhydrous magnesium sulfate. After the solvent was distilled off, 8.23 g of crude oil were obtained. The crude oil was subjected to flash column chromatography, whereby 6.72 g of (N-methyl-1,3-benzodioxol-5-ylamino)-N-t-butoxycarbonyl-S-methyl-L-cysteinamide were obtained (yield: 73%).

(KBr)$\nu_{max}$ cm$^{-1}$: 3272, 3044, 2972, 2916, 1708, 1658, 1608, 1538, 1486, 1448, 1430, 1392, 1366, 1328, 1282, 1250, 1226, 1168, 1104, 1060, 1034, 1016, 928, 872, 816, 654, 580.

$^1$H-NMR (CDCl$_3$) δ [200 MHz] ppm: 1.415(9H,s), 1.880(3H,s), 2.551(1H,dd, J=14,7Hz), 2.741(1H,dd,J=14,6.5 Hz), 3.249(3H,s), 4.50–4.57(1H,m), 5.281(1H,d,J=8 Hz), 6.027(2H,s), 6.70–6.90(3H,m).

MS m/z (%) [FAB]: 369(MH+), 313, 251.

EXAMPLE 8

Synthesis of (N-methyl-1,3-benzodioxol-5-ylamino)-S-methyl-L-cysteinamide hydrochloride After 6.323 g (17.183 mmol) of (N-methyl-1,3-benzodioxol-5-ylamino)-N-t-butoxycarbonyl-S-methyl-L-cysteinamide were dissolved in 100 ml of ethyl acetate, an excess of hydrochloric acid was ebulated. A precipitate so precipitated was collected by filtration, washed with ether, and then dried under reduced pressure, whereby 4.5 g of (N-methyl-1,3-benzodioxol-5-ylamino)-S-methyl-L-cysteinamide hydrochloride were obtained (yield: 86%).

IR (KBr)$\nu_{max}$ cm$^{-1}$: 3480, 2995, 1690, 1505, 1462, 1420, 1380, 1304, 1276 1256 1182 1140 1060 950, 840, 676.

$^1$H-NMR (CDCl$_3$) δ [200 MHz] ppm: 1.734(1H,s), 2.650(1H,dd,J=15,9.5 Hz), 2.897(1H,dd,J=15,4 Hz), 3.278(3H,s), 4.05–4.15(1H,m), 6.063(2H,s), 6.85–6.98(3H,m).

MS m/z (%) [FAB]: 269(M+-Cl).

EXAMPLE 9

Synthesis of (N-methoxycarbonylmethyl-1,3-benzodioxol-5-ylamino)-N-t-butoxycarbonyl-S-methyl-L-cysteinamide Dissolved in 10 ml of chloroform were 1.175 g (5 mmol) of N-t-butoxycarbonyl-S-methyl-L-cysteine, followed by the addition of 1.03 g (5 mmol) of dicyclohexylcarbodiimide (DDC) under ice cooling. The resultant mixture was stirred for 30 minutes. Then, 1.045 g (5 mmol) of methyl N-(1,3-benzodioxol-5-yl)-glycinate were added to the reaction mixture under ice cooling. The mixture so obtained was gradually heated and was stirred overnight at room temperature. Ethyl acetate was added to the solution, the resulting precipitate was removed and the solvent was then distilled off, so that 1.89 g of crude oil were obtained. The crude oil was subjected to flash column chromatography, whereby 1.172 g Of (N-methoxycarbonylmethyl-1,3-benzodioxol-5-ylamino)-N-t-butoxycarbonyl-S-methyl-L-cysteinamide were obtained (yield: 55%). In addition, 357 mg (23%) of the starting compound were recovered.

IR (KBr)$\nu_{max}$ cm$^{-1}$: 3412, 3288, 2980, 2924, 1754, 1710, 1668, 1504, 1488, 1426, 1394, 1368, 1336, 1280, 1248, 1208, 1170, 1106, 1068, 1036, 980, 934, 866, 816, 776, 730, 706, 656, 562, 510.

$^1$H-NMR (CDCl$_3$) δ [200 MHz] ppm: 1.416(9H,s), 1.897(3H,s), 2.537(1H,dd,J=14,7 Hz), 2.803(1H, dd,J=14,5.5 Hz), 3.747(3H,s), 4.247 (1H,d,J=17 Hz), 4.420(1H,d,J=17 Hz), 4.600(1H,m), 5.233(1H,d, J=8 Hz), 2.020(2H,s), 6.80–6.95(3H,m).

MS m/z (%) [FAB]: 427 (MH+).

EXAMPLE 10

Synthesis of (N-methoxycarbonylmethyl-1,3-benzodioxol-5-ylamino)-S-methyl-L-cysteinamide hydrochloride After 4.67 g (11 mmol) of (N-methoxycarbonylmethyl-1,3-benzodioxol-5-ylamino)-N-t-butoxycarbonyl-S-methyl-L-cysteinamide were dissolved in 100 ml of ethyl acetate, an excess of hydrochloric acid was ebulated. A precipitate so formed was collected by filtration, washed with ether and then dried under reduced pressure, whereby 3.3 g of (N-methoxycarbonylmethyl-1,3-benzodioxol-5-ylamino)-S-methyl-L-cysteinamide hydrochloride were obtained (yield: 83%).

IR (KBr)$\nu_{max}$ cm$^{-1}$: 3440, 2920, 1746, 1672, 1610, 1486, 1440, 1402, 1360, 1294, 1246, 1204, 1106, 1034, 982, 920, 870, 818, 730, 660.

$^1$H-NMR (CD$_3$OD) $\delta$ [200 MHz] ppm: 1.783(3H,s), 2.704(1H,dd,J=15,10 Hz), 2.955(1H, dd,J=15,4 Hz), 3.785(3H,s), 4.08–4.18(1H,m), 4.350(1H,d,J=17 Hz), 4.483(1H,d,J=17 Hz), 6.063(2H,s), 6.92–7.03(3H,m).

MS m/z (%) [FAB]: 7(M$^+$-Cl)

EXAMPLE 11

Synthesis of N-(1,3-dithiolan-2-ylidene)-1,3-benzodioxol-5-amine

Dissolved in 7 ml of dimethylsulfoxide were 1.00 g of 1,3-benzodioxol-5-amine and 437 $\mu$l of carbon disulfide, followed by the addition under ice cooling of a solution of 818 mg of potassium hydroxide in 1 ml of water. After the resulting mixture was stirred for 30 minutes, 687 $\mu$l of 1,2-dichloroethane were added, followed by stirring at 80° C. for 30 minutes. The reaction mixture was poured into ice water and then extracted twice with chloroform. The resulting organic layer was washed with water, shaken together with a saturated aqueous NaCl solution and then dried over anhydrous sodium sulfate. The solvent was distilled off, whereby 1.78 g of crude oil was obtained. The crude oil was purified by column chromatography (crude oil: 1.78 g, silica gel: MERCK 9385, 31 kg, column: 75 mm across×176 mm long, N$_2$ pressure: 0.3 kg/cm$^2$, developer: ethyl acetate:n-hexane=1:2), whereby 410 mg of N-(1,3-dithiolan-2-ylidene)-1,3-benzodioxol-5-amine were obtained as pale yellow crystals (yield: 23.5%).

Melting point: 125.0°–126.0° C.

IR (KBr)$\nu_{max}$ cm$^{-1}$: 1570, 1500, 1478, 1244, 1038.

$^1$H-NMR (CDCl$_3$) $\delta$ [200 MHz] ppm: 3.45–3.61(4H,m), 5.96(2H,s), 6.44(1H,dd,J=2.0, 8.3 Hz), 6.54(1H,d,J=2.0 Hz), 6.77(1H,d,J=8.3 Hz).

MS m/z (%) [EI-MS]: 239(100,M$^+$), 179(91), 92(67), 45(75).

Elemental analysis (as C$_{10}$H$_9$O$_2$NS$_2$): Calculated (%): C, 50.19, H, 3.79, N, 5.85. Found(%): C, 50.33, H, 3.80, N, 5.81.

EXAMPLE 12

Synthesis of methyl N-(1,3-benzodioxol-5-yl)-methoxycarbonylmethyl-carbamodithioate Methyl N-(1,3-benzodioxol-5-yl)-carbamodithioate (1.065 g) was added to a suspension of 120 mg of sodium hydride in 10 ml of THF and the resulting mixture was stirred at room temperature for 1 hour. The mixture was then added with 765 mg of methyl bromoacetate, followed by stirring overnight at room temperature. The reaction mixture was washed with water and extracted with ethyl acetate. The extract was then dried over anhydrous magnesium sulfate. After the solvent was distilled off, 1.17 g of reddish brown oil were obtained. The oil was subjected to chromatography on a silica gel column while using an ethyl acetate-hexane solvent, whereby 838 mg of methyl N-(1,3-benzodioxol-5-yl)-N-methoxycarbonylmethyl-carbamodithioate were obtained as pale yellow syrup (yield: 59%).

IR (NaCl)$\nu_{max}$ cm$^{-1}$: 2996, 2952, 2896, 1742, 1694, 1574, 1502, 1480, 1432, 1402, 1380, 1338, 1298, 1264, 1240, 1182, 1122, 1090, 1036, 994, 944, 922, 852, 812, 770, 718, 648.

$^1$H-NMR (CDCl$_3$) $\delta$ [200 MHz] ppm: 2.519(3H,s), 3.746(3H,s), 3.864(2H,s), 6.299(1H,dd,J=8,2 Hz), 6.405(1H,d,J=2 Hz), 6.745(1H,d,J=8 Hz).

MS m/z (%) [FD]: 285(M$^+$).

EXAMPLE 13

Synthesis of 3-(1,3-benzodioxol-5-yl)-2-(1,3-dithiol-2-ylidene)-3-oxo-propionic acid Isopropyl 3 1,3-benzodioxol-5-yl)-2-(1,3-dithiol-2-ylidene)-3-oxopropionate (7.53 g) was suspended in 290 ml of a methanol solution which contained 10% of sodium hydroxide and 10% of water. The suspension was refluxed for 2 hours. The reaction mixture was washed with ether and, under ice cooling, was acidified with concentrated hydrochloric acid. Crystals so precipitated were collected by filtration and then dried, whereby 5.36 g of 3-(1,3-benzodioxol-5-yl)-2-(1,3-dithiol-2-ylidene)-3-oxopropionic acid were obtained as ocherous crystals.

Melting point: 140.5° C. (decomposed).

IR (KBr)$\nu_{max}$ cm$^{-1}$: 1656, 1628, 1580, 1440, 1356, 1258, 1038.

$^1$H-NMR [(CD$_3$)$_2$SO] $\delta$ [200 MHz] ppm: 6.09(2H,s), 6.92(1H,d,J=8.3 Hz), 7.06(1H,d,J=2.0 Hz), 7.11(1H,dd,J=8.3,2.0 Hz), 7.53(1H,d,J=6.4 Hz), 7.62(1H,d,J=6.4 Hz)

MS m/z (%) [EI-MS]: 264(100), 149(32), 143(66).

EXAMPLE 14

Synthesis of methyl N-[3-(1,3-benzodioxol-5-yl)-2-(1,3-dithiol-2-ylidene)-3-oxopropionyl]glycinate Dissolved in 15.0 ml of N,N-dimethylformamide were 959 mg of 3-(1,3-benzodioxol-5-yl)-2-(1,3-dithiol-2-ylidene)-3-oxopropionic acid and 997 $\mu$l of triethylamine, followed by the addition of 469 mg of methyl glycinate hydrochloride. The reaction mixture was ice-cooled, to which 737 $\mu$l of diphenylphosphoryl azide were added. The resulting mixture was stirred for 3 hours and, while allowing its temperature to rise to room temperature, was stirred overnight. The reaction mixture was extracted with ethyl acetate. The resulting organic layer was washed with water, shaken together with a saturated aqueous NaCl solution and then dried over anhydrous sodium sulfate. The solvent was distilled off, whereby crude oil was obtained. The oil was purified by column chromatography (silica gel: "Fuji Davidson BW-300", column: 35 mm across×190 mm long, N$_2$ pressure: 0.3 kg/cm$^2$, developer: ethyl acetate:n-hexane=3:2) and then recrystallized from a mixed solvent of ethyl acetate and n-hexane, whereby 247 mg of methyl N-[3-(1,3-benzodioxol-5-yl)-2-(1,3-dithiol-2-ylidene)-3-oxopropionyl]glycinate were obtained as yellow crystals (yield: 21.6%).

Melting point: 168.5°–170.0° C.

IR (KBr)$\nu_{max}$ cm$^{-1}$: 1742, 1644, 1440, 1378, 1030.

$^1$H-NMR [(CD$_3$)$_2$SO]δ [200 MHz] ppm: 3.62(3H,s), 3.80(2H,d,J=5.6 Hz), 6.09(2H,s), 6.91(1H,d,J=8.1 Hz), 7.13(1H,d,J=1.7 Hz), 7.20(1H,dd,J=8.1,1,7 Hz), 7.37(1H,d,J=6.6 Hz), 7.46(1H,d,J=6.6 Hz), 8.23(1H,t,J=5.6 Hz)

MS m/z (%) [EI-MS]: 379(M+,57), 291(23), 149(100).

Elemental analysis (as C$_{16}$H$_{13}$O$_6$NS$_2$): Calculated (%): C, 50.65, H, 3.45, N, 5.69. Found(%): C, 50.81, H, 3.47, N, 3.81.

EXAMPLE 15

Synthesis of methyl L-N-[3-(1,3-benzodioxol-5-yl)-2-(1,3-dithiol-2-ylidene)-3-oxopropionyl]-S-methylcysteinate In 30.0 ml of N,N-dimethylformamide, 2.03 g of 3-(1,3-benzodioxol-5-yl)-2-(1,3-dithiol-2-ylidene)-3-oxopropionic acid and 1.10 ml of triethylamine, followed by the addition of 1.18 g of methyl S-methylcysteinate. The reaction mixture was ice-cooled, to which 1.56 ml of diphenylphosphoryl azide were added. The mixture was stirred for 5 hours and, while allowing its temperature to rise to room temperature, was stirred for 2 days. The reaction mixture was extracted with ethyl acetate. The resulting organic layer was washed with water, shaken together with a saturated aqueous NaCl solution and then dried over anhydrous sodium sulfate. The solvent was distilled off, whereby 4.39 g of crude oil were obtained. The oil was purified by column chromatography (crude oil: 4.39 g, silica gel: "Fuji Davidson BW-300", column: 50 mm across×198 mm long, N$_2$ pressure 0.3 kg/cm$^2$, developer: ethyl acetate:n-hexane=1:1) and then recrystallized from a mixed solvent of ethyl acetate and n-hexane, whereby 971 mg of methyl L-N-[3- 1,3-benzodioxol-5-yl)-2- 1,3-dithiol-2-ylidene)-3-oxopropionyl]-S-methylcysteinate were obtained as yellow needle crystals (yield: 33.6%).

Melting point: 148.0°–149.0° C.

IR (KBr)$\nu_{max}$ cm$^{-1}$: 1738, 1622, 1504, 1438, 1372, 1306, 1262, 1238, 1038.

$^1$H-NMR [(CD$_3$)$_2$SO] δ [200 MHz] ppm: 2.00(3H,s), 2.79(1H,dd,J=5.4,13.9 Hz), 2.86(1H,dd,J=5.4,13.9 Hz), 3.72(3H,s), 4.82(1H,ddd, J=5.4,5.4,7.3 Hz), 6.03(2H,S), 6.70(1H,d,J=7.3 Hz), 6.85(1H,dd,J=0.5,8.1 Hz), 7.06(1H,d,J=6.6 Hz), 7.16(1H,d,J=6.6 Hz), 7.21(1H,dd,J=0.5,1.7 Hz), 7.33(1H,dd,J=1.7,8.1 Hz)

MS m/z (%) [EI-MS]: 439(M+,13), 307(42), 291(38), 149(100)

Elemental analysis (as C$_{18}$H$_{17}$O$_6$NS$_3$): Calculated (%): C, 49.19, H, 3.90, N, 3.19. Found(%): C, 49.41, H, 3.99, N, 3.34.

EXAMPLE 16

Synthesis of isopropyl 3-(1,3-benzodioxole)-2-dimethylthiomethylidene-3-oxopropionate In 250 ml of dry tetrahydrofuran, 23.6 g of isopropyl 3- 1,3-benzodioxole)-3-oxopropionate were dissolved, followed by the addition of 8.30 g of sodium hydride under ice cooling and an argon stream. Further, 6.78 ml of carbon disulfide were also added. The reaction mixture was stirred for 30 minutes while its temperature was allowed to gradually rise to room temperature. Then, 14.1 ml of methyl iodide were added, followed by stirring at room temperature for one hour and a half hours. After the stirring, the reaction mixture was extracted with ethyl ether. The resulting organic layer was washed with water, shaken together with a saturated aqueous NaCl solution and then dried over anhydrous sodium sulfate. The solvent was distilled off, whereby 32.4 g of orange-colored crude oil were obtained. The oil was purified by column chromatography (silica gel: "Fuji Davidson BW-300", column: 100 mm across×272 mm long, N$_2$ pressure: 0.3 kg/cm$^2$, developer: ethyl acetate:n-hexane=1:8), whereby 6.34 g of isopropy 3-(1,3-benzodioxole)-2-dimethylthiomethylidene-3-oxopropionate were obtained as yellow oil (yield: 19.0%).

IR (NaCl)$\nu_{max}$ cm$^{-1}$: 1696, 1666, 1260

$^1$H-NMR (CDCl$_3$) δ [200 MHz] ppm: 1.11(6H,d,J=6.4 Hz), 2.26(3H,s), 2.51(3H,s), 5.03(1H,Sept.,J=6.4 Hz), 6.60(2H,s), 6.83(1H, d,J=8.6 Hz), 7.43(1H,d,J=1.7 Hz), 7.43(1H,dd, J=1.7,8.6 Hz)

MS m/z (%) [EI-MS]: 354(M+,25), 149(100)

SYNTHESIS EXAMPLE 1

Synthesis of methyl N-(3,4-methylenedioxyphenyl)dithiocarbamate 3,4-Methylenedioxyaniline (7.0 g) was dissolved in 100 ml of THF, to which 5.7 g of triethylamine and 5.8 g of carbon disulfide were added. The resulting mixture was stirred for 1 hour at room temperature. Then, 10.8 g of methyl iodide were added, followed by overnight stirring. The reaction mixture was washed with water and then extracted with ethyl acetate. The extract was dried over anhydrous magnesium sulfate. After the solvent was distilled off, 8.3 g or reddish brown crystals were obtained. The crystals were recrystallized from ethyl acetate, whereby 7.2 g of methyl N-(3,4-methylenedioxyphenyl)dithiocarbamate were obtained as colorless crystals.

Melting point: 114°–115° C.

IR (KBr)$\nu_{max}$ cm$^{-1}$: 3152, 3036, 2984, 2904, 1524, 1502, 1484, 1428, 1374, 1334, 1314, 1242, 1194, 1098, 1026, 972, 956, 926, 872, 808, 654, 620.

$^1$H-NMR (CDCl$_3$) δ [200MHZ] ppm: 2.629(3H,s), 6.014(2H,s), 6.810(2H,bs), 6.90(1H,bs), 9.0(1H,bs).

MS [EI]: 227(M+), 181, 180, 179, 121.

SYNTHESIS EXAMPLE 2

Synthesis of methyl 2-[N-(3,4-methylenedioxyphenyl)amino]acetate 3,4-Methylenedioxyaniline (30.7 g) was dissolved in 300 ml of dry tetrahydrofuran, followed by the addition of 10.7 g of sodium hydride (in oil, 60%) and 22.7 ml of methyl bromoacetate under ice cooling. Under an argon stream, the resultant mixture was stirred at room temperature for 2 days. The reaction mixture was extracted with ether. The organic layer so obtained was washed with water, shaken together with a saturated aqueous NaCl solution and then dried over anhydrous sodium sulfate. The solvent was distilled off, whereby reddish brown crystals were obtained. The crude crystals were decolored and then recrystallized from methanol, whereby 28.0 g of methyl 2-[N-(3,4-methylenedioxyphenyl)amino]acetate were obtained.

Melting point: 105.0°–106.0° C.

IR (KBr)$\nu_{max}$ cm$^{-1}$: 3404, 1730, 1446, 1346, 1222, 1036.

$^1$H-NMR (CDCl$_3$) δ [200 MHz] ppm: 3.77(3H,s), 3.85(2H,s), 4.08(1H,b), 5.86(2H,s), 6.03(1H,dd,J=2.4,8.3 Hz), 6.25(1H,d,J=2.4 Hz), 6.66(1H,d,J=8.3 Hz).

MS [EI]: 209(M+), 150.

FORMULATION EXAMPLE 1

| Tablets (Formulation) | |
|---|---|
| (1) Corn starch | 44 g |
| (2) Crystalline cellulose | 40 g |
| (3) Calcium carboxymethylcellulose | 5 g |
| (4) Light anhydrous silicic acid | 0.5 g |
| (5) Magnesium stearate | 0.5 g |
| (6) Compound obtained in Syn. Ex. 1 | 10 g |
| (TOTAL) | 100 g |

Procedures

Using the above formulation, the ingredients (1)–(6) were combined into an intimate mixture and then compression-molded by a tableting machine so that tablets weighing 200 mg each were obtained.

Each tablet contained 20 mg of the compound obtained in Synthesis Example 1. For adults, several doses per day are administered, to a total of 3–10 tablets daily.

FORMULATION EXAMPLE 2

| Tablets (Formulation) | |
|---|---|
| 1) Crystalline cellulose | 84.5 g |
| (2) Magnesium stearate | 0.5 g |
| (3) Calcium carboxymethylcellulose | 5 g |
| (4) Compound obtained in Syn. Ex. 2 | 10 g |
| (TOTAL) | 100 g |

Procedures

Using the above formulation, the ingredients (1) and (4) and a part of the ingredient (2) were combined into an intimate mixture, to which the ingredient (3) and the remaining part of the ingredient (2) were added, The resultant mixture was mixed and then compression-molded by a tableting machine so that tablets weighing 200 mg each were obtained. Each tablet contained 20 mg of the compound obtained in Synthesis Example 2. For adults, several doses per day are administered, to a total of 3–10 tablets daily.

FORMULATION EXAMPLE 3

| Tablets (Formulation) | |
|---|---|
| (1) Crystalline cellulose | 34.5 g |
| (2) 10% hydroxypropylcellulose solution in ethanol | 50 g |
| (3) Calcium carboxymethylcellulose | 5 g |
| (4) Magnesium stearate | 0.5 g |
| (5) Compound obtained in Syn. Ex. 1 | 10 g |
| (TOTAL) | 100 g |

Procedures

Using the above formulation, the ingredients (1), (2) and (5) were combined into an intimate mixture, kneaded in a usual manner, granulated by an extrusion granulating machine and then dried and crushed. With the powder so crushed, the ingredients (3) and (4) were mixed. The resulting mixture was then compression-molded by a tableting machine so that tablets weighing 200 mg each were obtained.

Each tablet contained 20 mg of the compound obtained in Synthesis Example 1. For adults, several doses per day are administered, to a total of 3–10 tablets daily.

FORMULATION EXAMPLE 4

| Granule (Formulation) | |
|---|---|
| (1) Corn starch | 84 g |
| (2) Magnesium stearate | 0.5 g |
| (3) Calcium carboxymethylcellulose | 5 g |
| (4) Light anhydrous silicic acid | 0.5 g |
| (5) Compound obtained in Syn. Ex. 2 | 10 g |
| (TOTAL) | 100 g |

Procedures

Using the above formulation, the ingredients (1)–(5) were combined into an intimate mixture, compression-molded by a tableting machine, ground by a grinding machine, and then sifted to obtain a granule.

Each gram of the granule contained 100 mg of the compound obtained in Synthesis Example 2. For adults, several doses per day are administered, to a total of 0.6–2 g daily.

FORMULATION EXAMPLE 5

| Granules (Formulation) | |
|---|---|
| (1) Crystalline cellulose | 55 g |
| (2) 10% hydroxypropylcellulose solution in ethanol | 35 g |
| (3) Compound obtained in Syn. Ex. 1 | 10 g |
| (TOTAL) | 100 g |

Procedures

Using the above formulation, the ingredients (1)–(3) were combined into an intimate mixture and then kneaded. The resulting mass was granulated by an extrusion granulating machine, dried and then sifted to obtain a granule.

Each gram of the granule contained 100 mg of the compound obtained in Synthesis Example 1. For adults, several doses per day are administered, to a total of 0.6–2 g daily.

FORMULATION EXAMPLE 6

| Capsules (Formulation) | |
|---|---|
| (1) Corn starch | 89.5 g |
| (2) Light anhydrous silicic acid | 0.5 g |
| (3) Compound obtained in Syn. Ex. 2 | 10 g |
| (TOTAL) | 100 g |

Procedures

Using the above formulation, the ingredients (1)–(3) were combined into an intimate mixture and then filled 200 mg by 200 mg in No. 2 capsules.

Each capsule contained 20 mg of the compound obtained in Synthesis Example 2. For adults, several doses per day are administered, to a total of 3-10 capsules daily.

FORMULATION EXAMPLE 7

| Injection (Formulation) | |
| --- | --- |
| (1) Injection-grade distilled water | 89.5 g |
| (2) Soybean oil | 5 g |
| (3) Soybean phospholipid | 2.5 g |
| (4) Glycerin | 2 g |
| (5) Compound obtained in Syn. Ex. 1 | 1 g |
| (TOTAL) | 100 g |

Procedures

Using the above formulation, the ingredient (5) was dissolved in a mixture of the ingredients (2) and (3). The resulting mixture was added with the ingredients (1) and (4), followed by emulsification. An injection was hence obtained.

We claim:

1. A benzodioxole derivative represented by the following formula (I):

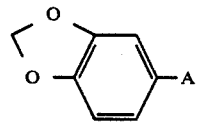

wherein A is:

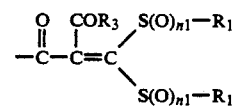

wherein $R_1$ and $R_2$ individually denote a lower alkyl group or are coupled together to form a $C_{1-3}$ alkylene group or —CH=CH—, $R_3$ is a hydroxyl, lower alkoxyl, amino or alkyl substituted amino group, and $n_1$ stands for an integer of 0-2.

2. A hepatopathy improver comprising:
   as an effective ingredient, the benzodioxole derivative of formula I according to claim 1 and a pharmaceutically acceptable carrier.

* * * * *